(12) United States Patent
Lu et al.

(10) Patent No.: US 7,964,750 B2
(45) Date of Patent: Jun. 21, 2011

(54) METHOD FOR SYNTHESIZING 9,10-DIHYDRO-9-OXA-10-PHOSPHAPHE-NANTHRENE-10-OXIDE OR A DERIVATIVE THEREOF

(75) Inventors: Ling Lu, Taipei Hsien (TW); Kai-Chiang Huang, Taoyuan Hsien (TW); Kuan-Chieh Tseng, Pintung Hsien (TW); Chung-Ning Fan, Taoyuan Hsien (TW); Yu-Cheng Lee, Miaoli Hsien (TW); Tien-Wen Lo, Taoyuan Hsien (TW); Yu-Chin Lee, Taipei (TW)

(73) Assignee: UFC Corporation, Taipei (TW)

( * ) Notice: Subject to any disclaimer, the term of this patent is extended or adjusted under 35 U.S.C. 154(b) by 0 days.

(21) Appl. No.: 12/535,897

(22) Filed: Aug. 5, 2009

(65) Prior Publication Data
US 2011/0034717 A1 Feb. 10, 2011

(51) Int. Cl.
*C07F 9/6571* (2006.01)
(52) U.S. Cl. ............................. 558/82; 558/122; 562/19
(58) Field of Classification Search ................... 558/82, 558/122; 562/19
See application file for complete search history.

(56) References Cited

U.S. PATENT DOCUMENTS

| | | | |
|---|---|---|---|
| 4,086,206 A | 4/1978 | Saito et al. | |
| 5,391,798 A | 2/1995 | Kleiner | |
| 5,481,017 A * | 1/1996 | Kleiner .......................... | 558/82 |
| 5,650,530 A | 7/1997 | Buysch et al. | |
| 5,821,376 A | 10/1998 | Rathfelder et al. | |
| 6,107,506 A | 8/2000 | Saito et al. | |

FOREIGN PATENT DOCUMENTS

| | | |
|---|---|---|
| CN | 101108864 A | 1/2008 |
| DE | 19505352 | 3/1996 |
| DE | 19505353 | 3/1996 |
| EP | 582957 A1 | 2/1994 |
| EP | 739896 | 2/1998 |

OTHER PUBLICATIONS

Merriam-Webster Online Dictionary entry for "derivative", (http://www.merriam-webster.com/dictionary/derivative), last accessed May 12, 2010.*
Wang, Chun-Shan et al., Synthesis and properties of epoxy resins containing 2-(6-oxid-6H-debenz[c,e][1,2] oxaphosphorin-6-y1) 1,4-benzenediol, Polymer, vol. 39: pp. 5819-5826, 1998, Elsevier Science Ltd.

* cited by examiner

*Primary Examiner* — Joseph R Kosack
*Assistant Examiner* — Matthew P Coughlin
(74) *Attorney, Agent, or Firm* — WPAT, P.C.; Anthony King

(57) ABSTRACT

A method for synthesizing 9,10-dihydro-9-oxa-10-phosphaphenanthrene-10-oxide or its derivatives has a step of introducing 6-chloro-6H-dibenz[c,e][1,2]oxaphosphorin or its derivative, an acid compound and water into a reacting chamber to form an organic layer having 9,10-dihydro-9-oxa-10-phosphaphenanthrene-10-oxide or its derivative and an aqueous layer. Because the acid compound is from an external source and has a catalyzing effect, employing the method can prevent side reaction from occurring and increase yield of 9,10-dihydro-9-oxa-10-phosphaphenanthrene-10-oxide or its derivative. Furthermore, the method is a one-pot operation of hydrolysis, dehydration and cyclization, so the method does not require purification of intermediates. Therefore, the method is time- and cost-saving and requires less organic solvent, resulting in less pollution to the environment.

14 Claims, 5 Drawing Sheets

METHOD FOR SYNTHESIZING 9,10-DIHYDRO-9-OXA-10-PHOSPHAPHE-NANTHRENE-10-OXIDE OR A DERIVATIVE THEREOF

BACKGROUND OF THE INVENTION

1. Field of the Invention

The present invention relates to a method for synthesizing 9,10-dihydro-9-oxa-10-phosphaphenanthrene-10-oxide or its derivatives, particularly to a method using a single reaction vessel and does not require isolation of intermediates.

2. Description of the Prior Arts 9,10-dihydro-9-oxa-10-phosphaphenanthrene-10-oxide, which may be referred to as 'DOPO', is a compound broadly used for antibacterial agents, antioxidants, fading resistant agents and fire retardants. The compound is not halide and thus can be used as a flame-retarding monomer without negative effects on the environment. Furthermore, the compound is used universally for synthetic fibers, plastic materials used for electronic devices, copper clad laminate on printed circuit boards, packaging materials for semiconductors, and photosensitive materials to increase flame-retardant capability of materials.

Since 1972, a method for synthesizing DOPO has been constantly researched and improved in patents such as U.S. Pat. Nos. 4,086,206, 5,391,798, 5,481,017, 5,650,530, 5,821,376, 6,107,506, EP 739896, EP0582957A1, DE 19505352, DE 19505353, CN 101108864A and in the journal Polymer, 39,5819-5826, 1998. The method for synthesizing DOPO comprises steps of: providing 6-chloro-6H-dibenz[c,e][1,2] oxaphosphorin; hydrolyzing 6-chloro-6H-dibenz[c,e][1,2] oxaphosphorin to form 2-(hydroxy-biphenyl-2-y1)-phosphinic acid by a hydrolytic process; and dehydrating 2-(hydroxy-bipheny1-2-y1)-phosphinic acid to form DOPO at high temperature under vacuum to remove water.

The hydrolytic processes can be classified as basic, solvent, direct, ice or alcohol hydrolysis, and are described below.

A. basic hydrolysis: 6-chloro-6H-dibenz[c,e][1,2]oxaphosphorin is put into a basic solution and to which is added hydrogen sulfate to form 2-(hydroxy-biphenyl-2-yl)-phosphinic acid that is incubated at high temperature under 90 Kpa to form DOPO.

B. solvent hydrolysis: 6-chloro-6H-dibenz[c,e][1,2]oxaphosphorin is added to an organic solvent for hydrolysis and crystallization and incubated at high temperature under vacuum to form DOPO.

C. direct hydrolysis: 6-chloro-6H-dibenz[c,e][1,2]oxaphosphorin is added to equal moles of deionized water at a temperature between 80 and 130° C. for 3 to 10 hours for hydrolysis and incubated at high temperature under vacuum to form DOPO.

D. ice hydrolysis: 6-chloro-6H-dibenz[c,e][1,2]oxaphosphorin is added over ice to be hydrolyzed to form 2-hydroxy-bipheny1-2-y1)-phosphinic acid that is then dehydrated to form DOPO.

E. alcohol hydrolysis: 6-chloro-6H-dibenz[c,e][1,2]oxaphosphorin is added to a molar equivalent of deionized water and an appropriate amount of alcohol to facilitate contact between 6-chloro-6H-dibenz[c,e][1,2]oxaphosphorin and water, to accelerate the hydrolytic process and form 2-(hydroxy-biphenyl-2-yl)-phosphinic acid that is incubated at high temperature under vacuum to form DOPO.

However, the above-mentioned hydrolytic processes have great drawbacks for the following reasons:

(1) Reaction times of the hydrolytic processes are too long.

(2) Each hydrolytic process requires purification of intermediates and further dehydration and cyclization reaction to form final product. Therefore, the processes are complicated.

(3) For some of the processes, highly-polar organic solvents are required to manufacture and purify products. Therefore, said processes easily cause environmental pollution.

(4) Since each process requires use of great quantities of deionized water, a lot of waste, which pollutes the environment, is generated.

(5) Since each process requires separation of intermediates, yields are low.

(6) Each process has multiple purifying steps to manufacture DOPO, so purity and color of 9,10-dihydro-9-oxa-10-phosphaphenanthrene-10-oxide are not easy to be controlled.

(7) The processes are complicated, so manufacturing costs of product are high.

(8) Each process consumes much energy.

To overcome the shortcomings, the present invention provides a method for synthesizing 9,10-dihydro-9-oxa-10-phosphaphenanthrene-10-oxide or a derivative thereof to mitigate or obviate the aforementioned problems.

SUMMARY OF THE INVENTION

The main objective of the present invention is to provide a method for synthesizing 9,10-dihydro-9-oxa-10-phosphaphenanthrene-10-oxide (DOPO) or its derivative using a single reaction vessel that does not require isolation of intermediates.

A method for synthesizing DOPO or its derivatives in accordance with the present invention has a step of mixing 6-chloro-6H-dibenz[c,e][1,2]oxaphosphorin or its derivative and an acid compound in water to form an organic layer having 9,10-dihydro-9-oxa-10-phosphaphenanthrene-10-oxide or its derivative and an aqueous layer. Due to the acid compound having a catalytic effect, employing the method to synthesize DOPO or its derivatives can prevent side reactions from occurring and increase yield of 9,10-dihydro-9-oxa-10-phosphaphenanthrene-10-oxide or its derivatives. Furthermore, the method is conducted in a single reaction vessel of hydrolysis, dehydration and cyclization, so the method does not require purification of intermediates. Therefore, the method can reduce time-consumption and cost and requires less organic solvent, therefore reducing the environmental impact.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
FIG. 1 is a flow chart of a method for synthesizing 9,10-dihydro-9-oxa-10-phosphaphenanthrene-10-oxide (DOPO) or its derivative in accordance with the present invention.

With reference to FIG. 1, a method for synthesizing a compound of formula 2 comprises steps of:

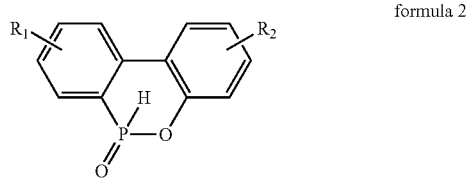

formula 2 providing a compound 1 of formula 1; and

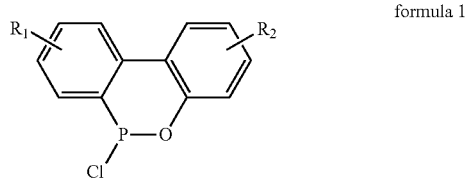

formula 1 mixing compound 1 and an acid compound in water to form an organic layer having a compound of formula 2 and an aqueous layer at an appropriate temperature; wherein $R_1$ and $R_2$ are independently selected from the group consisting of hydrogen, $C_1$-$C_8$ alkyl, $C_1$-$C_8$ alkoxy, $C_1$-$C_8$ silyl, and benzyl.

Preferably, $R_1$ and $R_2$ are both hydrogen.

Preferably, the compound 1 and the acid compound are mixed in an equivalent portion between 1 to 5 and 1 to 1.

The acid compound may be an inorganic acid.

Preferably, the inorganic acid is selected from the group consisting of sulfuric acid, hydrochloric acid, phosphoric acid, hydrobromic acid, hydroiodic acid, hydrofluoric acid, carbonic acid, boric acid, polyphosphoric acid and chromic acid.

The acid compound may be an organic acid.

More preferably, the organic acid is selected from the group consisting of benzenesulfonic acid, p-toluenesulfonic acid, trifluoroacetic acid, formic acid, acetic acid and glacial acetic acid.

Preferably, the water is deionized water.

Most preferably, the acid compound and water are mixed at a ratio of the acid compound to water between 1 to 1 and 1 to 10 by weight.

Preferably, the step of mixing compound 1 and the acid compound in water is performed at a reaction temperature between 40 and 80° C.

Preferably, the method for synthesizing a compound of formula 2 further has steps of separating the organic layer and the aqueous layer and drying the organic layer to obtain DOPO.

More preferably, the step of separating the organic layer and the water layer is performed at a separating temperature between 60 and 100° C.

More preferably, drying the organic layer comprises distilling the organic layer at a distilling temperature under reduced pressure.

Most preferably, the distilling temperature is between 160 and 185° C. and the reduced pressure is between 0.3 and 1.0 mbar.

The acid compound is mixed with 6-chloro-6H-dibenz[c,e][1,2]oxaphosphorin (formula 1) in water to obtain a reaction intermediate of 2-(hydroxy-biphenyl-2-yl[)]-phosphinic acid (formula 3). Then, 2-(hydroxy-biphenyl-2-yl[)]-phosphinic acid is dehydrated by the acid compound to form 9,10-dihydro-9-oxa-10-phosphaphenanthrene-10-oxide (formula 2), as shown in the following chemical equation:

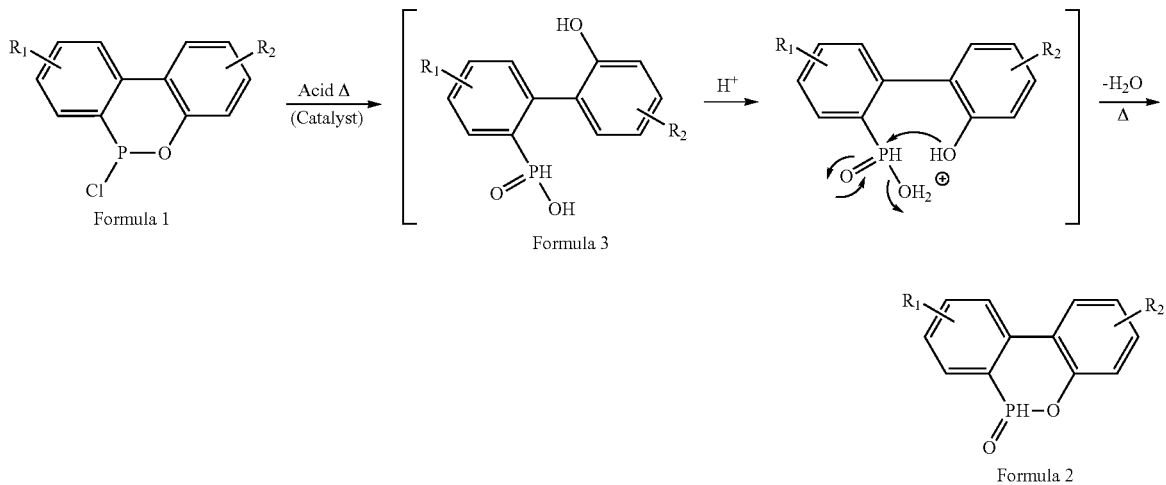

The acid compound hydrolyzes 6-chloro-6H-dibenz[c,e][1,2]oxaphosphorin in water to form 2-(hydroxy)-biphenyl-2-yl-phosphinic acid and then removal of a water molecule and a hydrogen proton is carried out by reduced pressure distillation forms 9,10-dihydro-9-oxa-10-phosphaphenanthrene-10-oxide having consistent color and high purity.

EXAMPLES

The following examples further illustrate the present invention but are not to be construed as limiting the invention as defined in the claims appended hereto.

(1) Measuring Method
(a) Purity Analysis

Purity of DOPO was examined with Shimadzu HPLC. The parameters and conditions of HPLC are as shown in the following Table 1:

TABLE 1

| | |
|---|---|
| Equipment | Shimadzu HPLC |
| Column | ZORBAX Eclipse XDB-C8 Column 4.6 × 250 mm |
| Flow Rate | 1.0 mL/min |
| Mobile Phase | 100% methanol (anhydrous) |
| Detector | UV at 280 nm |
| Column Temp. | 30° C. |
| Sample Solution | 50 mg/10 mL methanol (anhydrous) |
| Inject volumes | 5 μL | formula 1(%)(area %)=formula 2 (area %)+formula 3 (area %).

Retention time of formula 2 (rt) is 2.64 mins.
Retention time of formula 3 (rt) is 1.82 mins.

Example 1

Reaction without Acid Compound 10g of 6-chloro-6H-dibenz[c,e][1,2]oxaphosphorin (0.0426 moles) and 20g of deionized water were introduced into a reacting chamber and stirred for 5 minutes to form a solution. The solution was heated to 100° C. for 4 hours and 20ml toluene was added and then the solution was cooled to 30° C. to separate out a solid. The solution was filtered through a filter paper to obtain the solid. The solid was added to 20 ml ethanol for recrystallization to obtain a white crystalline powder. The crystalline powder was filtrated and subjected to a reduced pressure distillation at 160° C. under 0.3 mbar to obtain 6.91 g of white solid of 9,10-dihydro-9-oxa-10-phosphaphenanthrene-10-oxide [yield: 75%, color: 30 Hazen, purity: 95.35% (yield formula 2:formula 3=95.35%: 4.35%), melting point: 115.76° C. (temp. of DSC)].

Example 2

Figure 2:
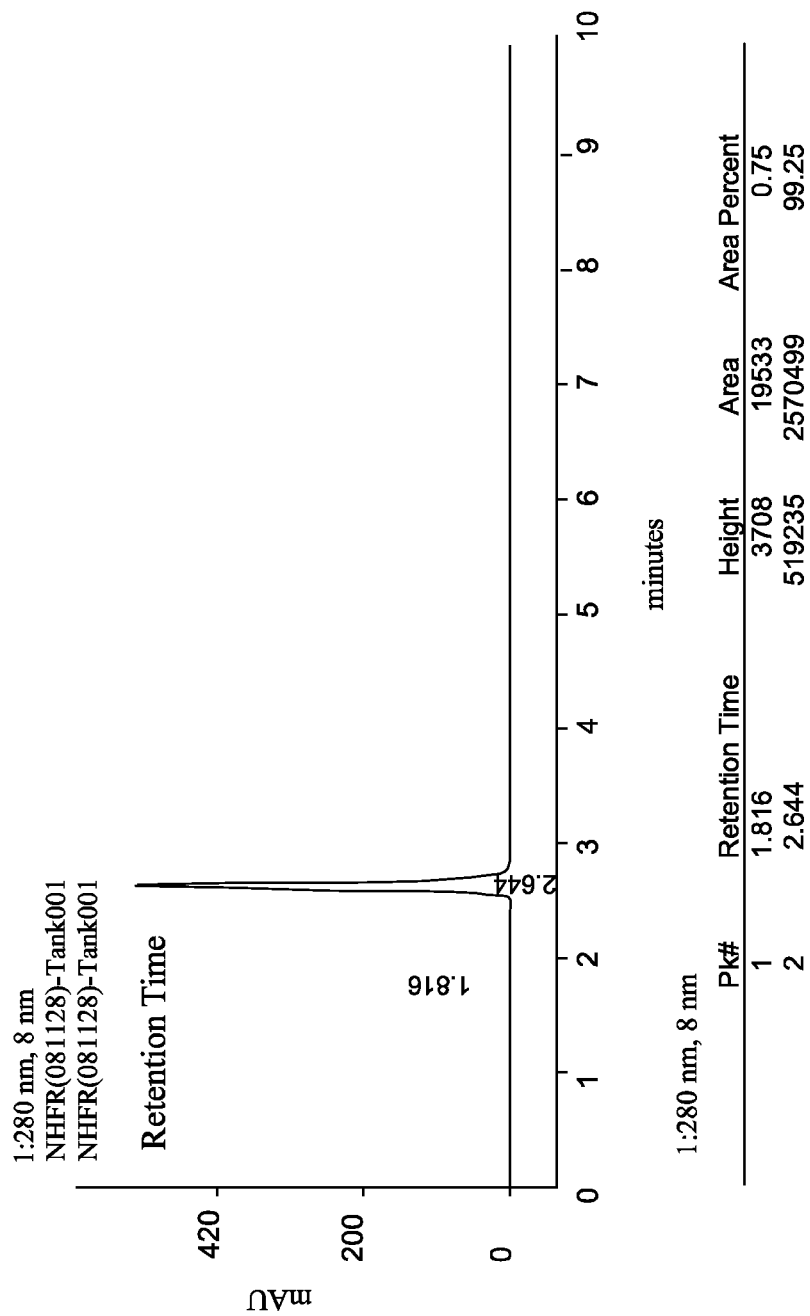
FIG. 2 is an HPLC diagram of DOPO.
Figure 3:
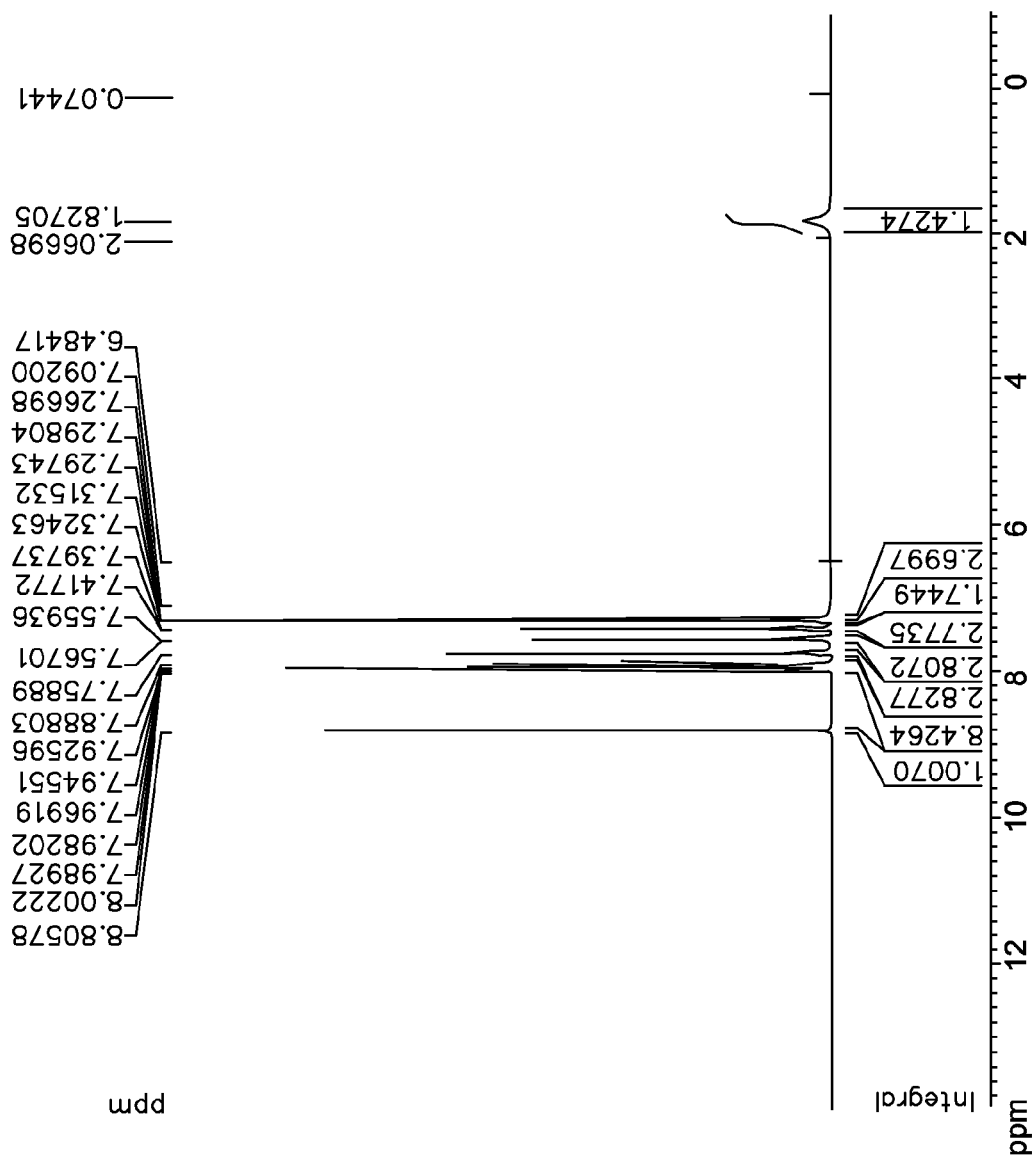
FIG. 3 is an $H^1$-NMR spectrum of DOPO.
Figure 4:
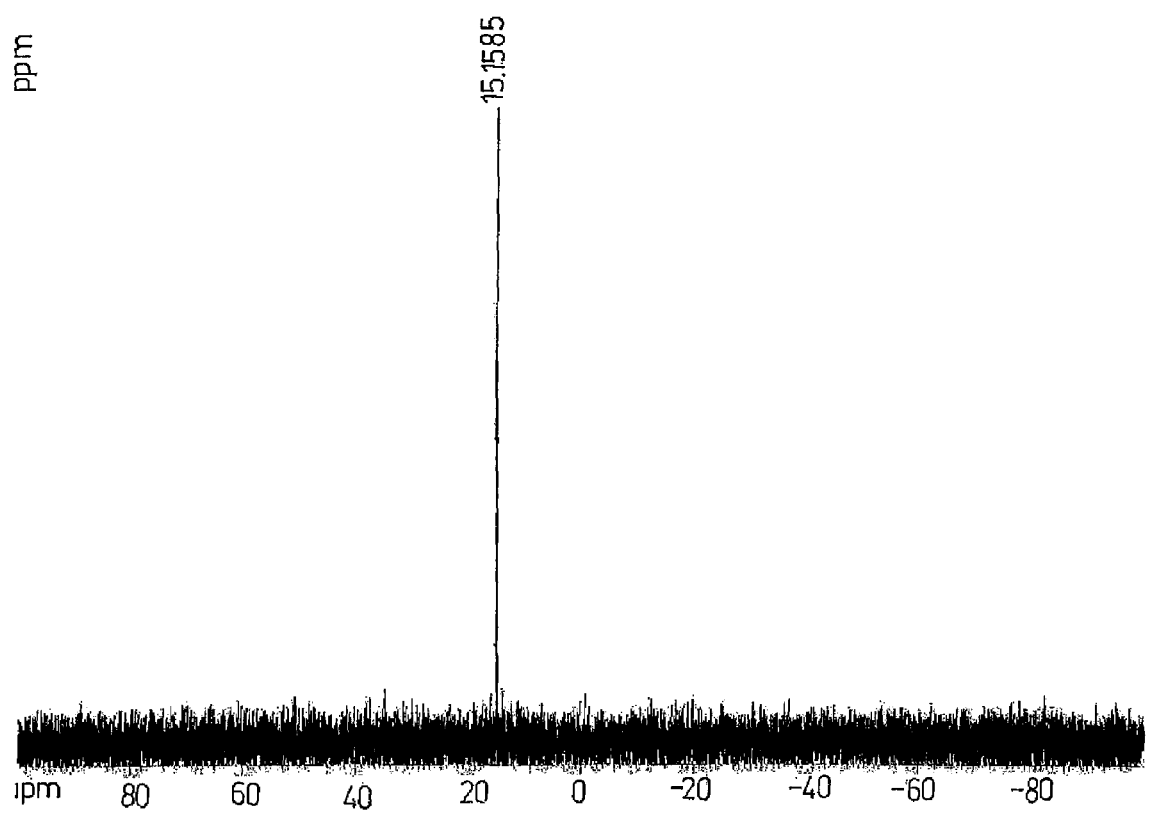
FIG. 4 is a $^{13}P$-NMR spectrum of DOPO.
Figure 5:
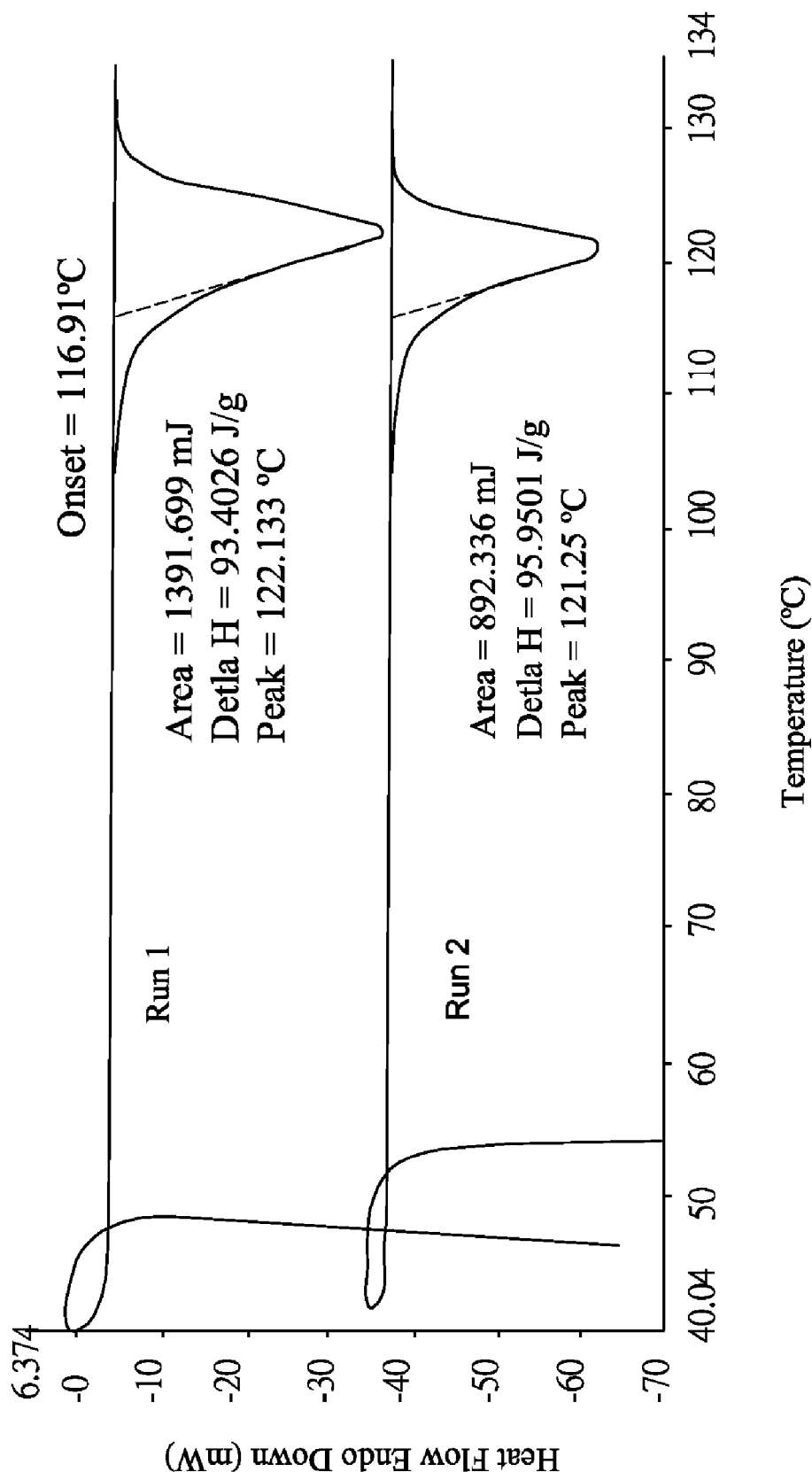
FIG. 5 is a differential scanning calorimeter diagram of DOPO.

Reaction with Hydrochloric Acid 10g of 6-chloro-6H-dibenz[c,e][1,2]oxaphosphorin (0.0426 moles), 1.2g hydrochloric acid (0.0335 moles) and 2.1g of water were introduced into a reacting chamber and stirred for 5 minutes to form a solution. The solution was heated at 80° C. for 1 hour to obtain an organic layer and an aqueous layer. The organic layer was maintained at 80° C., separated from the aqueous layer, put into another reacting chamber and subjected to a reduced pressure distillation at 165° C. under 0.3mbar to obtain 9.03g of white solid of 9,10-dihydro-9-oxa-10-phosphaphenanthrene-10-oxide (as shown in FIGS. 2 to 4) [yield: 98%, color: 8 Hazen, purity: 99.25% (formula 2:formula 3=99.25%: 0.75%), melting point: 122.13° C. (DSC peak)](as shown in FIG. 5).

Example 3

Reaction with Sulfuric Acid 10 g of 6-chloro-6H-dibenz[c,e][1,2]oxaphosphorin (0.0426 moles), 3.286 g sulfuric acid (0.0335 moles) and 3 g of water were introduced into a reacting chamber and stirred for 5 minutes to form a solution. The solution was heated at 80° C. for 5 hours to obtain an organic layer and an aqueous layer. The organic layer was maintained at 80° C., separated from the aqueous layer, put into another reacting chamber and subjected to a reduced pressure distillation at 165° C. under 0.3 mbar to obtain 8.94g of white solid of 9,10-dihydro-9-oxa-10-phosphaphenanthrene-10-oxide [yield: 97%, color: 10 Hazen, purity: 96.03% (formula 2:formula 3=96.03%: 2.6%), melting point: 118.61° C. (DSC peak)].

Example 4

Reaction with Phosphoric Acid 10g of 6-chloro-6H-dibenz[c,e][1,2]oxaphosphorin (0.0426 moles), 3.28g phosphoric acid (0.0335 moles) and 3g of water were introduced into a reacting chamber and stirred for 5 minutes to form a solution. The solution was heated at 80° C. for 1.5 hours to obtain an organic layer and an aqueous layer. The organic layer was maintained at 80° C., separated from the aqueous layer, put into another reacting chamber and subjected to a reduced pressure distillation at 165° C. under 0.3 mbar to obtain 8.85g of white solid of 9,10-dihydro-9-oxa-10-phosphaphenanthrene-10-oxide [yield: 96%, color: 12 Hazen, purity: 97.97% (formula 2:formula 3=97.97%: 1.44%), melting point: 119.97° C. (DSC peak)].

Example 5

Reaction with Glacial Acetic Acid 10 g of 6-chloro-6H-dibenz[c,e][1,2]oxaphosphorin (0.0426 moles), 2.01 g glacial acetic acid (0.0335 moles) and 3 g of water were introduced into a reacting chamber and stirred for 5 minutes to form a solution. The solution was heated at 80° C. for 3 hours to obtain an organic layer and an aqueous layer. The organic layer was maintained at 80° C., separated from the aqueous layer, put into another reacting chamber and subjected to a reduced pressure distillation at 165° C. under 0.3 mbar to obtain 7.83g of white solid of 9,10-dihydro-9-oxa-10-phosphaphenanthrene-10-oxide [yield: 85%, color: 14 Hazen, purity: 98.1% (formula 2:formula 3=98.1%: 1.9%), melting point: 119.59° C. (DSC peak)].

TABLE 2

Table showing product foregoing experiments

| | Ex. 1 - None | Ex. 2 - HCl | Ex. 3 - $H_2SO_4$ | Ex. 4 - $H_3PO_4$ | Ex. 5 - $CH_3COOH$ |
|---|---|---|---|---|---|
| Product (g) | 6.91 | 9.03 | 8.94 | 8.85 | 7.83 |
| Yield (%) | 75 | 98 | 97 | 96 | 85 |
| Color (Hazen) | 30 | 8 | 10 | 12 | 14 |
| Purity (%) | 95.35 | 99.25 | 96.03 | 97.97 | 98.1 |
| melting point (° C.) | 115.76 | 122.13 | 118.61 | 119.97 | 119.59 |

Since the acid compound catalyzes the above-mentioned reaction, the method deters against side reaction occurring and increases yield of 9,10-dihydro-9-oxa-10-phosphaphenanthrene-10-oxide. Furthermore, the method uses one reaction vessel for hydrolysis, dehydration and cyclization, so the method does not require purification of intermediates. Moreover, the method does not require washing with organic solvent and therefore reduces environmental impact of the method. Therefore, the method can be time- and cost-saving and requires less organic solvent, resulting in less pollution to the environment.

Even though numerous characteristics and advantages of the present invention have been set forth in the foregoing description, together with details of the structure and function of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A method for synthesizing a compound of formula 2, comprising steps of:

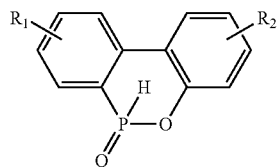

formula 2 providing a compound 1 of formula 1; and

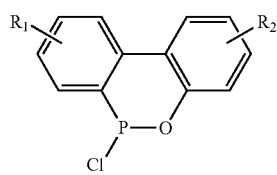

formula 1 introducing the compound 1, an acid compound and water into a reacting chamber to form an organic layer having a compound of formula 2 and an aqueous layer, wherein $R_1$ and $R_2$ are independently selected from the group consisting of hydrogen, $C_1$-$C_8$ alkyl, $C_1$-$C_8$ alkoxy, $C_1$-$C_8$ silyl and benzyl.

2. The method for synthesizing a compound of formula 2 as claimed in claim 1, further comprising steps of:
separating the organic layer and the aqueous layer; and
drying the organic layer to obtain a compound of formula 2.

3. The method for synthesizing a compound of formula 2 as claimed in claim 1, wherein $R_1$ and $R_2$ are both hydrogen.

4. The method for synthesizing a compound of formula 2 as claimed in claim 1, wherein the acid compound is an inorganic acid.

5. The method for synthesizing a compound of formula 2 as claimed in claim 4, wherein the inorganic acid is selected from the group consisting of sulfuric acid, hydrochloric acid, phosphoric acid, hydrobromic acid, hydroiodic acid, hydrofluoric acid, carbonic acid, boric acid, polyphosphoric acid and chromic acid.

6. The method for synthesizing a compound of formula 2 as claimed in claim 1, wherein the acid compound is an organic acid.

7. The method for synthesizing a compound of formula 2 as claimed in claim 6, wherein the organic acid is selected from the group consisting of benzenesulfonic acid, p-toluenesulfonic acid, trifluoroacetic acid, formic acid, acetic acid and glacial acetic acid.

8. The method for synthesizing a compound of formula 2 as claimed in claim 1, wherein the compound 1 and the acid compound are mixed in an equivalent portion between 1 to 5 and 1 to 1.

9. The method for synthesizing a compound of formula 2 as claimed in claim 1, wherein the water is deionized water.

10. The method for synthesizing a compound of formula 2 as claimed in claim 1, wherein the acid compound is dissolved in water between 1 to 1 wt % and 1 to 10 wt %.

11. The method for synthesizing a compound of formula 2 as claimed in claim 1, wherein a reaction temperature of mixing compound 1 and the acid compound in water is between 40 and 80° C.

12. The method for synthesizing a compound of formula 2 as claimed in claim 2, wherein a separating temperature of separating the organic layer and the aqueous layer is between 60 and 100° C.

13. The method for synthesizing a compound of formula 2 as claimed in claim 2, wherein the step of drying the organic layer comprises distilling the organic layer at a distilling temperature under a reduced pressure.

14. The method for synthesizing a compound of formula 2 as claimed in claim 13, wherein the distilling temperature is between 160 and 185° C. and the reduced pressure is between 0.3 and 1.0 mbar.

* * * * *